United States Patent [19]

Groves

[11] Patent Number: 5,186,936
[45] Date of Patent: Feb. 16, 1993

[54] PACKING MATERIAL FOR TREATMENT OF INFECTIONS

[75] Inventor: Michael J. Groves, Lake Forest, Ill.

[73] Assignee: Board of Trustees of the University of Illinois, Chicago, Ill.

[21] Appl. No.: 563,394

[22] Filed: Aug. 6, 1990

[51] Int. Cl.$^5$ ............ A01N 25/08; A01N 25/24; A61K 9/70; A61K 47/36

[52] U.S. Cl. ................ 424/435; 424/407; 424/409; 424/422; 424/423; 424/426; 424/443; 424/488; 433/217.1; 514/777; 514/779; 514/788

[58] Field of Search ............ 424/426, 435, 443, 407, 424/409, 422, 423, 488; 433/217.1; 514/777, 779, 788

[56] References Cited

U.S. PATENT DOCUMENTS

| | | | |
|---|---|---|---|
| 4,175,326 | 11/1979 | Goodson | 433/80 |
| 4,568,536 | 2/1986 | Kronenthal et al. | 514/772 |
| 4,685,883 | 8/1987 | Jernberg | 433/215 |
| 4,764,377 | 8/1988 | Goodson | 424/435 |
| 5,002,769 | 3/1991 | Friedman | 424/422 |

OTHER PUBLICATIONS

Article by Michael Friedman et al. entitled Sustained-Release Delivery Systems for Treatment of Dental Diseases, Pharmaceutical Research, vol. 7, No. 4, 1990, pp. 313–317.

One page Article pertaining to Alza Company dated Jan. 20, 1988.

Article by A. A. Badwan et al. entitled A Sustained Release Drug Delivery System Using Calcium Alginate Beads, Drug Dev. Ind. Pharm. 11, No. 2–3, 239–56, (1985)-Abstract.

Article by H. N. Newman entitled Modes of Application of Anti-Plaque Chemicals, J. Clin Periodontal, 1986, 13:965–974.

Article by Noguchi et al. entitled New Method for Local Drug Delivery Using Resorbable Base Material in Periodontal Therapy, Bull, Tokyo Med. Dent. Univ., 31: 145–153 (1984).

Article by Dunn et al. entitled Biodegradable Fibers for the Controlled Release of Tetracycline in Treatment of Periodontal Disease, Proveed, Intern, Symp. Control Rel. Bioact. Mater. 14 (1987) pp. 259 and 260.

Article by W. G. Wade et al. entitled Comparison of in vitro Activity of Niridazole, Metronidazole and Tetracycline Against Subgingival Bacteria in Chronic Periodontitis, Journal of Applied Bacteriology 1987, 63,. 455–457.

Article by R. W. Baker et al. entitled A Controlled Release Drug Delivery System for the Periodontal Pocket, Proceed Intern. Symp. Control. Rel. Bioact. Mater. 15 (1988) pp. 238a–238b.

Article by Johansen et al. entitled In Vitro Evaluation of Dermal Prodrug Delivery—Transport and Bioconversion of a Series of Aliphatic Esters of Metronidazole, International Journal of Pharmaceutics 32 (1986) 199–206.

Article by Johnsen et al. entitled A Comparison of the Chemical Stability and the Enzymatic Hydrolysis of a Series of Aliphatic and Aromatic Ester Derivatives of Metronidazole, International Journal of Pharmaceutics, 26 (1985) 227–241.

Article of Masato Minabe et al. entitled Application of a Local Drug Delivery System to Periodontal Theraph . . . J. Periodontol, vol. 60, Feb. 1989, pp. 113–117.

*Primary Examiner*—Thurman K. Page
*Assistant Examiner*—Carlos Azpuru
*Attorney, Agent, or Firm*—Marshall, O'Toole, Gerstein, Murray & Bicknell

[57] ABSTRACT

A packing material for the treatment of infections, particularly of the teeth and gums. A biocompatible, polymeric carrier material, typically calcium alignate, has dispersed therein an antibiotic ester which typically defines at least one ester group of 10 to 18 carbon atoms per molecule. The antibiotic ester is present in the polymeric carrier in an initial concentration sufficient to allow the continuous, controlled release of at least an inhibitory concentration of free antibiotic as a hydrolysis product from the antibiotic ester. The rate of release of free antibiotic is influenced by the presence of bacterial lipase, so that a higher concentration of infectious bacteria causes the release of higher concentrations of free antibiotic, hydrolyzed from the ester, in a feedback loop.

16 Claims, No Drawings

PACKING MATERIAL FOR TREATMENT OF INFECTIONS

BACKGROUND OF THE INVENTION

Goodson U.S. Pat. No. 4,764,377 describes an intrapocket drug delivery device for the treatment of periodontal disease. The therapeutic agent delivery device may be packed into a periodontal pocket formed in the gum tissue against the root of the tooth where a chronic infection such as pyorrhea exists. The packing material of the Goodson patent is a string-like polymeric material which carries a concentration of an antibiotic such as tetracycline for controlled release of the tetracycline over a period of time into the periodontal cavity. By this technique, a continuous delivery of an antibiotic may be provided for the elimination of chronic infection.

Additionally, the Goodson patent teaches a diffusion limiting surface about a stringlike therapeutic agent delivery device, apparently to control the rate of diffusion of tetracycline or other antibiotic from the plastic material in which it resides.

As one disadvantage of the above system, the antibiotic which diffuses out of the polymeric carrier will rapidly disperse out of the periodontal pocket by diffusion through the tissue. Also, the rate of antibiotic diffusion is of course constant and predictable whether or not there is a substantial concentration of bacteria present o not.

It would be desirable to provide a controlled release vehicle for antibiotics in a packing material for the treatment of infections in which the diffusion rate of antibiotic can be effectively slowed, but that the concentration of free antibiotic present can increase in a manner which is dependent upon the concentration of bacteria present. Thus, in a chronic situation when bacterial infections may appear and disappear, such a packing material would tend to retain its supply of antibiotic when the concentration of harmful bacteria present was very low, but the release of free antibiotic would increase as the concentration of bacteria increased. This would form a long-lived, self-regulating system to keep the area containing the packing material substantially free of infection.

Such a system is provided in accordance with this invention, in which a minimum, desired concentration of free antibiotic is released under circumstances where the bacteria concentration is low, but in the event of significant infection the release of antibiotic from the packing material of this invention can increase in response to the infectious conditions. Thus, the packing material of this invention can have a longer useful life when placed in an infection-prone tissue pocket or the like, since under conditions of low bacterial concentration a low concentration of free antibiotic is released. However, but when the need arises, higher amounts of antibiotic are released in response to higher concentrations of bacteria present.

Additionally, in this invention the antibiotic may be stored in a prodrug form which, if it diffuses from the packing material, is less permeable through tissue, so that it tends to be retained in the body cavity into which it is released.

DESCRIPTION OF THE INVENTION

In this invention, a packing material is provided for the treatment of infections, particularly infections of the teeth and gums, although it is contemplated to be also useful in other situations as well. By this invention, a biocompatible, polymeric carrier material is provided, carrying therein an antibiotic ester which defines at least one ester group of typically 10 to 18 carbon atoms per molecule.

The term "antibiotic ester" relates to any conventional, medically available antibiotic which has at least one hydroxyl or carboxylic acid group which is capable of undergoing an esterification reaction with an appropriate carboxylic acid or alcohol having 10 to 18 carbon atoms, so that the antibiotic ester defines a pendent ester group which is the residue of such carboxylic acid or alcohol having 10 to 18 carbon atoms. The antibiotic ester serves as a prodrug which may be activated by hydrolysis of the ester group from the antibiotic to restore it to the original antibiotic form.

The antibiotic ester can diffuse from the biocompatible polymeric carrier after implantation in a body tissue before its hydrolysis, or the antibiotic ester may be hydrolyzed within the polymeric carrier, and the free antibiotic can diffuse out into the body tissue. Typically, the antibiotic ester that diffuses from the carrier tends to have lower tissue permeability than the free antibiotic, so it tends to remain in the body cavity in which the polymeric carrier material resides until it is hydrolyzed. The effect of this is to decrease the outward diffusion of the antibiotic that is present for greater dosage efficiency in the body cavity over a long term period.

The antibiotic ester is present in the polymeric carrier, typically being distributed throughout the mass of the polymeric carrier either as a solid solution or as small particles of antibiotic ester, in an initial concentration which is sufficient to allow the continuous, controlled release of typically at least an inhibitory concentration of free antibiotic as a hydrolysis product from the antibiotic ester in response to the presence of bacterial lipase. Many bacteria which are associated with infection produce a lipase enzyme which serves to promote the hydrolysis of ester groups. Thus, the release of free antibiotic will be dependent at least in part on the titer of bacteria present around the packing material packed in a body cavity. If the concentration of bacteria is low, the presence of bacterial lipase is correspondingly low, and the release of free antibiotic from the packing material will be low. If infectious conditions are present, the concentration of bacterial lipase will be higher, resulting in a more rapid rate of ester group cleavage, so that a higher concentration of free antibiotic will be present.

Preferably, the minimum inhibitory concentration of free antibiotic which is continuously released by the packing material of this invention will be essentially equivalent in its antibacterial effect to at least 3 micrograms per ml. of the antibiotic metronidazole, which is a preferred antibiotic for use in this invention. As stated above, in the presence of infectious levels of bacteria concentration, the release by diffusion and hydrolysis of free antibiotic may result in a concentration substantially higher than the above, while a diminution of the concentration of bacteria through the effect of the antibiotic will cause a spontaneous reduction in the concentration of free antibiotic present. Thus, the packing material of this invention releases free antibiotic in an economical manner which can be tailored to an optimum clinical program for the treatment of chronic infections, particularly those of the type found in gum disease.

Preferably, the concentration of antibiotic ester in the biocompatible, polymeric carrier may range from about 10 to 150 percent by weight, based on the polymeric carrier present.

The biocompatible polymers used herein may be any of a wide variety, such as those described in the above cited Goodson patent. Preferably calcium or magnesium alginate is used, or other hydrogels such as pectin, chitosan, or chitin.

The palmitate (16 carbon) ester of metronidazole is a preferred antibiotic ester for use in this invention, while the current most preferred biocompatible, polymeric carrier material comprises calcium alginate. Metronidazole palmitate disperses relatively easily in calcium alginate and is stable therein, but for the diffusion and hydrolysis processes which result in free antibiotic delivery in accordance with this invention. If desired, free antibiotic may also be added to the polymeric carrier to provide a bolus of initial antibiotic release, since the free antibiotic will diffuse out of the system faster than antibiotic ester, to develop an immediate concentration of antibiotic in the tissue adjacent the implanted packing material until the slower diffusion and hydrolysis processes of the antibiotic ester get under way.

It should be understood that while antibiotic esters in which the ester group has fewer carbon atoms, (6 or less) are known for use in the medical field, their purpose was to improve the topical delivery of a drug by means of esterification so that its transmissibility through the skin would increase. In this invention, the use of higher ester groups tends to decrease the diffusability of the esterified drugs through tissue, to cause an increase in the concentration of antibiotic in the tissue pocket in which the packing material resides during use.

Metronidazole palmitate is released from a calcium alginate polymeric carrier material in high quantities, and reacts in the presence of lipase enzymes to provide free metronidazole with a hydrolysis rate generally proportional to the enzyme concentration. At lower enzyme concentrations on the order of no more than 0.4 milligrams per ml. of liquid media, a lag period may be noted of several hours before the hydrolysis reaction is noted, showing that the antibiotic may be spared, and retained adjacent the packing material, when the tissue surrounding the packing material is not infected. Other esters of metronidazole and other antibiotics in accordance with this invention can also provide similar results.

Likewise, the twenty four hour release of metronidazole from metronidazole palmitate diffused in calcium alginate strings is substantially directly proportional to the loading of metronidazole alginate in the string.

The polymeric carrier may be of any desired shape, preferably being of string or fibrous form. The string or fiber used as the polymeric carrier material containing an antibiotic ester may be a solid string or fiber, or a hollow string or fiber having a lumen. If desired, the lumen may contain a relatively large supply of antibiotic ester in accordance with this invention or another medicament, or a mixture thereof. The inner core of the fiber, (the terms "string" and "fiber" being synonymous) may contain as a polymeric carrier a hydrogel which defines ionic polymer units of one charge, positive or negative, and, of course, accompanying simple ions of the other charge such as calcium or chloride. The fiber also may define an outer coating which comprises a hydrogel which defines ionic polymer units of the opposite charge to that of the hydrogel of the inner core. The antibiotic ester is substantially carried in the inner core, and/or in a lumen defined in the inner core, while the outer coating acts as a controlled release barrier to limit generation of free antibiotic. Thus, by control of the outer coating, the antibiotic release rates of the packing material of this invention may be controlled to conform to a large variety of desirable clinical programs.

For example, the inner core may comprise an alginate salt such an calcium or magnesium alginate, while the outer coating comprises a material such as pectin, chitosan, or chitin.

Alternatively, the packing material of this invention may be a fiber which comprises an inner core of a hydrogel polymeric carrier which defines ionic polymer units, for example calcium alginate. The same fiber may have an outer coating which comprises a mixture of 70 to 95 parts by weight of poly(lysine) or other related polypeptide, and 5 to 30 parts by weight when applied of a polyol-type plasticizer for the poly(lysine). The term "when applied" means that the mixture of poly(lysine) and plasticizer as described above is the mixture when it is just applied to the inner core of the fiber. Upon contact with water, the polyol-type plasticizer will of course dissolve away, and it may evaporate upon storage, resulting in an outer coating which acts as a controlled release barrier to limit generation of the free antibiotic.

The polyol plasticizer is present primarily to define small apertures in the outer coating, which serves to permit a limited amount of release of the antibiotic ester or free antibiotic, since the plasticizer, if it still remains, will be quickly leached away after implantation in a tissue pocket. It thus follows that higher concentrations of polyoltype plasticizers will result in an outer coating that is more permeable to the antibiotic and antibiotic ester than an outer coating with lower concentrations of polyol plasticizer, so that predetermined release characteristics may be built into the system.

Examples of polyol-type plasticizers which may be used include glycerine, sorbitol, and/or polyethylene glycol. In this situation, the preferred hydrogel for the inner core is calcium alginate.

As yet another embodiment, such a fiber may also carry an outermost, hydrophilic alginate layer such as sodium or potassium alginate, to provide a smooth, hydrophilic surface. Additionally, the outer layer may be calcium or magnesium alginate.

Additional ingredients which may be added to the packing materials of this invention include an agent for either x-ray or optical visibility such as barium sulfate or fluorescein. Likewise, as stated before, free antibiotic may be added.

Additionally, the above-described packing materials which include an inner core and an outer coating may be used for other controlled-diffusion purposes besides those specifically described in this invention, for example, for the controlled diffusion of free antibiotic without esterification, or for the controlled diffusion of other medicaments and nutrients such as vitamins, hormones, heparin, and the like at an implantation site.

The above disclosure and the examples below are offered for illustrative purposes only, and are not intended to limit the scope of the invention of this application, which is as described in the claims below.

EXAMPLE 1

Thirty ml. of 0.5 percent (w/v) sodium alginate solution was prepared. To this solution was added, with vigorous mixing, an amount of metronidazole palmitate sufficient to provide to the solution a quantity of 210 micrograms per ml. of metronidazole upon complete hydrolysis of the ester. Metronidazole palmitate is made by an esterification reaction between metronidazole and palmitic acid.

The solution was well mixed, and one ml. portions of the suspension of metronidazole palmitate in the solution were drawn up into a syringe equipped with a 16 gauge needle. The one ml. portions were then injected through the needle in a steady stream into a one molar calcium chloride solution, to form strings of calcium alginate about 7 cm. in length and 0.5 mm. in diameter, which strings contained the dispersed metronidazole palmitate.

After allowing the strings to remain in the calcium chloride solution for 5 minutes, each string was removed, rinsed in 0.1 percent calcium chloride solution, and placed in 0.1 percent (w/v) CHES solution, followed by soaking in a solution of 0.35 percent (w/v) poly(lysine) and 10 to 15 percent (w/v) glycerine for 3 minutes. CHES solution is $2_1$N-cyclohexylamine ethane sulfonic acid, manufactured by Sigma Chemical Company. Then, the calcium alginate strings were soaked again in the 0.1 percent calcium chloride solution, followed by the CHES solution. Then, the string was immersed in 0.15 percent (w/v) sodium alginate solution for a further 3 minutes. Following this, the strings were removed and dried in air before packaging.

When portions of the above strings are implanted into periodontal pockets in the gum surrounding a portion of teeth which have been afflicted with pyorrhoea, the hydrated strings or fibers release free metronidazole on a continuous basis for at least a period of days, but in which the release of free metronidazole is more rapid when infection is present, and of a reduced rate when the infectious symptoms recede, for the long term treatment of gum disease.

EXAMPLE 2

Sodium alginate (0.5 percent w/w) was dissolved in double distilled water by stirring at room temperature. Using a motor driven syringe containing 10 ml. of an aqueous dispersion of 210 micrograms per ml. of metronidazole palmitate is extruded through a 16 gauge needle into an excess (100 ml.) of 0.1 percent w/v calcium chloride solution. The cord which forms from the alginate material by this process is allowed to equilibrate for 5 minutes before removing carefully and immersing in 100 ml. of 0.1 percent CHES solution for an additional five minutes.

The resulting cord was then washed by immersion an excess of 0.1 percent calcium chloride solution for 30 minutes before transferring it to about 50 ml. of 0.035 percent w/v poly(lysine) solution for three minutes with careful stirring. The cord was then washed with 0.1 percent calcium chloride solution again, followed by a second immersion in a fresh 0.1 percent portion of CHES solution for five minutes.

Then, the thread was transferred to a 0.1 percent sodium alginate solution for three minutes before air drying at room temperature for 24 hours. The thread was finally dried by desiccation over an anhydrous calcium chloride for 48 hours at room temperature.

Equivalent results are obtained to the results of Example 1 when the cord or string is placed into a periodontal pocket in the gum of a patient next to teeth which have been infected with pyorrhoea.

It is possible to prepare the above cords of alginate having lengths up to about 70 cm. by this method, with the cords containing on the order of 0.43–0.44 milligrams of metronidazole palmitate per cm. of length.

EXAMPLE 3

Calcium alginate thread was made in accordance with the method of Example 2, up through the step prior to immersion in 100 ml. of 0.1 percent CHES solution for the first time. Then, the resulting cord was transferred to a 1 percent solution of Chitosan (Protan Protosan MV) in double distilled water and allowed to stand for 15 minutes. The cord was withdrawn and air dried for 24 hours before drying over anhydrous calcium chloride for 48 hours.

The resulting cord exhibited the characteristic described in this application of providing a controlled release of metronidazole palmitate, which can be converted in the presence of lipase enzyme into metronidazole.

That which is claimed is:

1. A packing material for the treatment of infections, particularly of the teeth and gums, which comprises:
    a biocompatible, polymeric carrier material having therein an metronidazole ester which defines at least one ester group of 10 to 18 carbon atoms per molecule, said metronidazole ester being present in said polymeric carrier in an initial concentration sufficient to allow the continuous, controlled release of at least a bacterial growth inhibitory concentration of free antibiotic as a hydrolysis product from said antibiotic ester in response to the presence of bacterial lipase.

2. The packing material of claim 1 in which said antibiotic ester is metronidazole palmitate.

3. The packing material of claim 1 in which said polymeric carrier is calcium alginate.

4. The packing material of claim 1 in which said polymeric carrier comprises a fiber.

5. The packing material of claim 4 in which said fiber comprises an inner core containing a hydrogel which defines ionic polymer units of one charge, said fiber also defining an outer coating which comprises a hydrogel which defines ionic polymer units of the opposite charge to that of the hydrogel of the inner core, said antibiotic ester being substantially carried in said inner core, said outer coating acting as a controlled release barrier to limit release of free antibiotic.

6. The packing material of claim 5 in which said inner core comprises calcium alginate and said outer coating comprises a material selected from the group consisting of pectin, chitosan, and chitin.

7. The packing material of claim 4 in which said fiber comprises an inner core containing a hydrogel which defines anionic polymer units plus an outer coating which comprises a mixture of 70 to 95 parts by weight of poly(lysine) and 5 to 30 parts by weight when applied of a polyol-type plasticizer for said poly(lysine), said outer coating acting as a controlled release barrier to limit generation of free antibiotic.

8. The packing material of claim 7 in which said hydrogel of the inner core is calcium alginate.

9. The packing material of claim 1 in which said inhibitory concentration of free antibiotic is essentially equivalent in effect to 3 micrograms per ml. of metronidazole.

10. A packing material for the treatment of infections of the teeth and gums, which comprises:
   a biocompatible, polymeric carrier material having carried therein metronidazole palmitate, said metronidazole palmitate being present in said polymeric carrier in an initial concentration sufficient to allow the continuous, controlled release of at least an inhibitory concentration of free antibiotic as a hydrolysis product from said metronidazole palmitate in response to the presence of bacterial lipase, said polymeric carrier comprising an alginate.

11. The packing material of claim 10 in which said polymeric carrier is calcium alginate.

12. The packing material of claim 11 in which said inhibitory concentration of free antibiotic is essentially equivalent in effect to 3 micrograms per ml. of metronidazole.

13. The packing material of claim 12 in which said polymeric carrier comprises a fiber.

14. The packing material of claim 13 in which said fiber comprises an inner core containing said calcium alginate plus an outer coating which comprises a mixture of 70 to 95 parts by weight of poly(lysine) and 5 to 30 parts by weight of a polyol-type plasticizer for said poly(lysine), said outer coating acting as a controlled release barrier to limit generation of free antibiotic from said metronidazole palmitate.

15. The packing material of claim 13 in which said fiber comprises an inner core containing said alginate plus an outer coating which comprises a polylactate, said fiber carrying an outermost, hydrophilic alginate layer.

16. The packing material of claim 10 in which said inhibitory concentration of free antibiotic is three micrograms per ml. of metronidazole.

* * * * *